(12) United States Patent
Elasri et al.

(10) Patent No.: US 6,468,220 B1
(45) Date of Patent: Oct. 22, 2002

(54) ECHOGRAPHY PROBE AND ACCESSORIES

(75) Inventors: Jack Elasri, Labastide Saint-Sernin; Dany Carre, Naintre; Frederic Peyre, Lherm; Leandre Pourcelot, Veigne; Jean-Marc Gregoire, Mettray, all of (FR)

(73) Assignee: Pierre Fabre Dermo-Cosmetique SA, Boulogne-Cedex (FR)

( * ) Notice: Subject to any disclaimer, the term of this patent is extended or adjusted under 35 U.S.C. 154(b) by 0 days.

(21) Appl. No.: 09/600,226

(22) PCT Filed: Jun. 26, 1998

(86) PCT No.: PCT/FR98/01371

§ 371 (c)(1),
(2), (4) Date: Aug. 21, 2000

(87) PCT Pub. No.: WO99/03695

PCT Pub. Date: Jan. 28, 1999

(30) Foreign Application Priority Data

Jan. 14, 1998 (FR) .............................................. 98 00314

(51) Int. Cl.⁷ ................................................ A61B 8/14
(52) U.S. Cl. ........................ 600/459; 600/446; 73/633; 73/618
(58) Field of Search ................................. 600/446, 459; 73/67.8, 615, 620, 602, 633

(56) References Cited

U.S. PATENT DOCUMENTS 4,120,291 A * 10/1978 Paton et al. .................. 73/618
4,917,096 A * 4/1990 Englehart et al. ........... 600/446

* cited by examiner

*Primary Examiner*—Marvin M. Lateef
*Assistant Examiner*—Ruby Jain
(74) *Attorney, Agent, or Firm*—Harrison & Egbert

(57) ABSTRACT

A probe including a body having a main chamber receiving an assembly for transmitting and receiving an ultrasonic wave. The assembly is mounted on a frame driven in reciprocating motion by a driving motor. The chamber is closed by a probe tip having a slot made of a liquid impermeable solid element which is permeable to the acoustic wave transmitted by the acoustic transducer and toward the acoustic transducer. A reciprocating motion of the acoustic transducer is a translating movement parallel to the slot such that the ultrasonic beam is normal at the slot.

10 Claims, 2 Drawing Sheets

ECHOGRAPHY PROBE AND ACCESSORIES

BACKGROUND OF THE INVENTION

1. Field of the Invention

The invention presented here has the object of a probe notably for ultrasonic scanning, which can be mainly used in dermatology, provided with an electroacoustic monotransducer driven by a back and forward movement in an acoustic coupling medium.

2. Description of the Related Art

Mechanical probes for ultrasonic scanning, generally consisting of a tubular body, can be gripped by hand and consist of a chamber in which an electroacoustic transducer is installed. To this tubular body, in the extension of the chamber, a tip of the probe is connected and provided with a slot for the passage of acoustic waves emitted by the transducer. Finally, a coupling medium such as a homogenous liquid is placed in the chamber. This liquid forms the propagation medium to the slot of the probe tip of ultrasonic waves emitted by the electroacoustic transducer. The slot of the probe tip is generally in the form of a more or less thin wall impermeable to the coupling liquid but permeable, in varying degrees, to the acoustic wave. In other devices, notably those specifically designed for scanning the skin and more generally for scanning at low depth, the slot of the probe tip is in the form of an opening. The reason for this arrangement is essentially that the scanning at low depth requires an ultrasonic wave at a higher frequency and that this wave is very easily attenuated by the wall of the slot. However, it should be known that most pathologies become located on the face in the zones which can be jagged, such as the nose and the lobe of the ears. For this reason, the use of a probe with an open acoustic slot can pose numerous problems such as that of keeping constant the quantity of the acoustic coupling liquid in the probe. The use of a wall, for example, in the form of a membrane to constitute the acoustic slot (preferred solution among practicing doctors) creates the problem of the attenuation of the wave and the repetition echoes between the slot and the acoustic transducer. These repetition echos are often a product of artifacts masking useful information and making it impossible to interpret the images. This problem can be solved if the acoustic beam is oblique relative to the slot as instructed in the prior art. In this case, the reflection echo is no longer sent back towards the acoustic transducer and the artifact no longer appears on the image formed. As a consequence, users have some problems in positioning the probe in a precise manner relative to the region to be scanned.

It is important that the signal coming from the probe be directly usable. Due to the pendular movement of the monotransducer, the output signal must be handled by a system having a format change. Such a system has the disadvantage of slowing down the display rate and reducing the size of the input slot.

Finally, due to their high frequencies, the return signals are easily damaged by the different zones crossed, land notably by the coupling medium.

BRIEF SUMMARY OF THE INVENTION

The purpose of the invention presented here is to solve the problems mentioned above by implementing a new type of ultrasonic scanning probe designed to emit an output signal that can be used immediately in order to form a rectangular image.

Another purpose of the invention presented here is to propose an acoustic probe in which the slot of the tip of the probe is made up of a wall and whose acoustic beam is normal to this slot for an, easy positioning without artifacts being able to appear in the image formed.

Another goal of the invention presented here is to propose a probe for which the attenuation of the return signal in the coupling medium is reduced.

For this purpose, the low depth scanning probe, consisting of a tubular body in which a main chamber is arranged to accommodate an assembly for the emission and reception of an ultrasonic wave formed from an acoustic monotransducer, installed on a mount driven in a back and forth movement in the main chamber by a movement transmission united with a drive motor mounted in a secondary chamber arranged in the tubular body and separated from the main chamber by a partitioning element, the main chamber being blocked in an airtight manner by a probe tip that contains an acoustic slot made of a solid element, impermeable to the acoustic coupling liquid introduced into the main chamber and permeable to the acoustic wave emitted by the transducer in the direction from the anatomical region to be scanned and permeable to the return wave reflected by the anatomical region in the direction of the acoustic monotransducer, characterized essentially in that the back and forth movement of the assembly for the emission and reception of the acoustic wave is a movement in parallel translation to the acoustic slot of the probe tip, the ultrasonic beam staying normal to the slot of the tip of the probe.

By this device, the signal coming from the probe can be used directly so well that no mechanism for changing the format is required for the formation of a rectangular image that can then be displayed at a higher rate.

According to another characteristic of the invention, the distance between the assembly for the emission and reception of the acoustic wave and the acoustic slot is equal to or greater than: $P_{max} \cdot c1/c2$ where:
- $P_{max}$ is the maximum depth of scanning
- c1 is the speed of the acoustic wave in the coupling medium,
- c2 is the speed of the acoustic wave in the anatomical region to be scanned.

This particularly advantageous arrangement of the invention eliminates any risk of an artifact in the image formed and guarantees a good distinction of the structure of the dermis and epidermis.

According to another characteristic of the invention, the coupling medium is essentially water.

This device eliminates the risk of al large attenuation of the signal.

BRIEF DESCRIPTION OF THE SEVERAL VIEWS OF THE DRAWINGS

Other advantages and characteristics of the invention appear in reading the description of a preferred embodiment form in reference to the attached drawings.

DETAILED DESCRIPTION OF THE INVENTION

Figure 1:
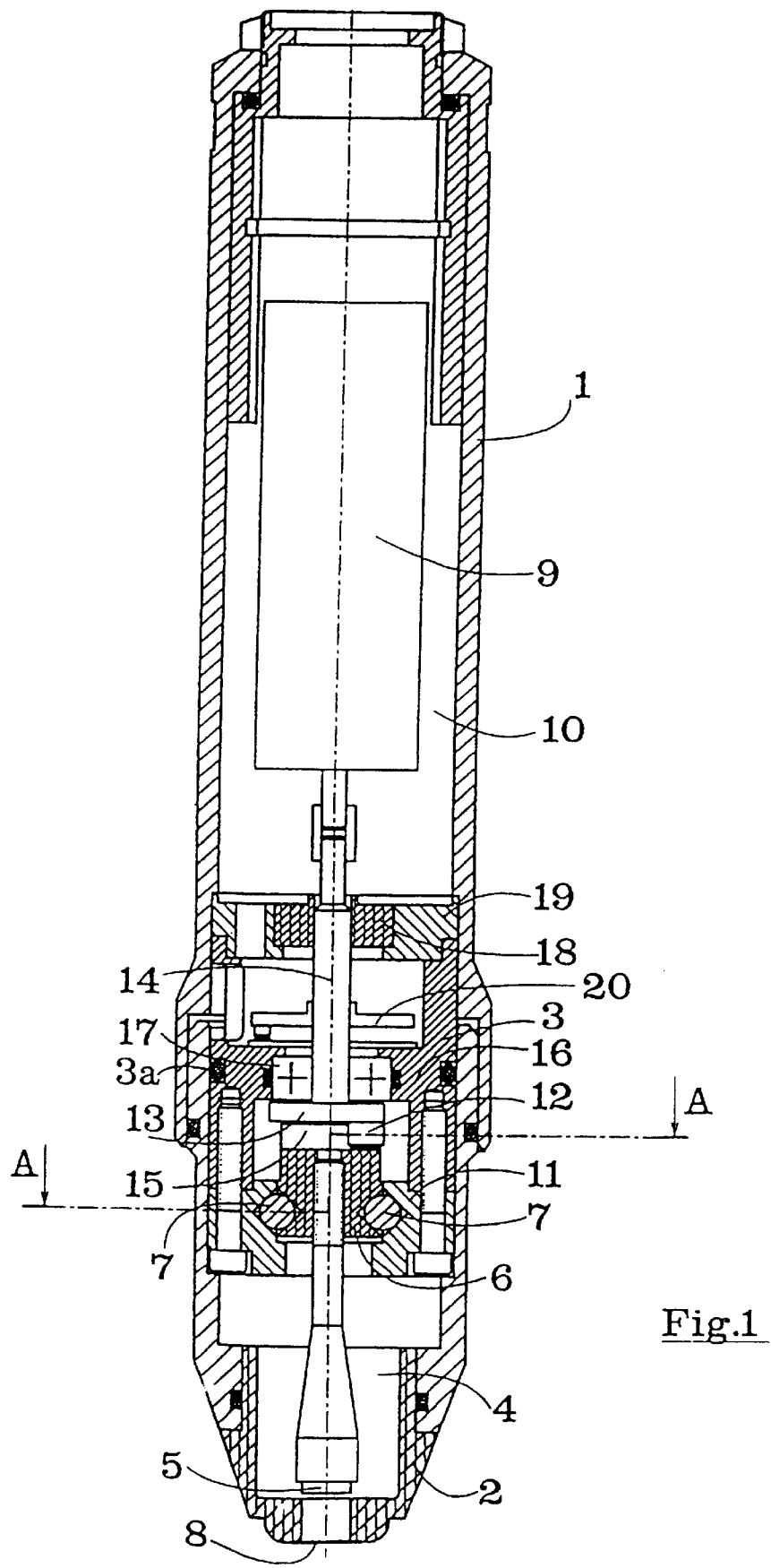
FIG. 1 is a longitudinal section view of the probe according to the invention.
Figure 2:
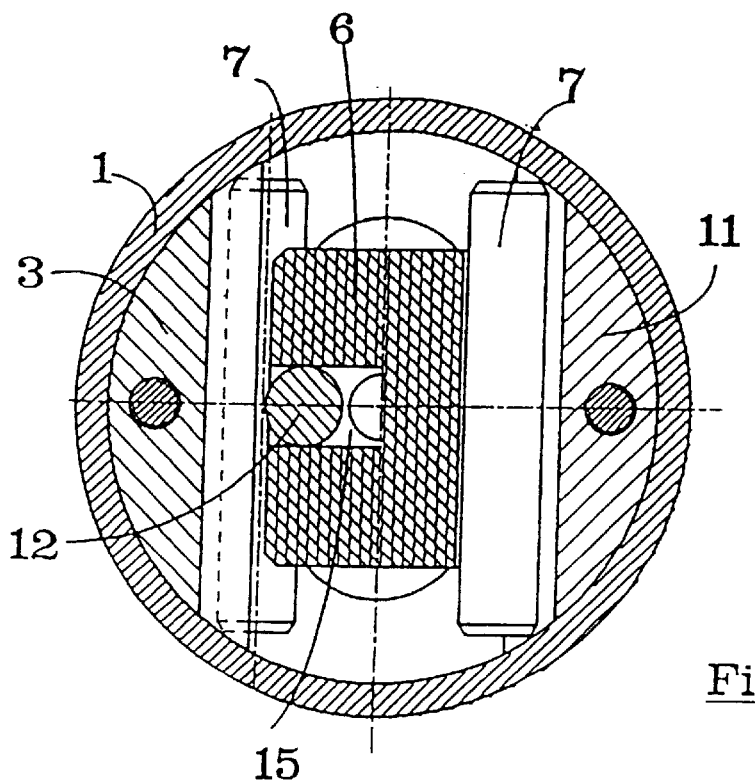
FIG. 2 is a section view along the dashed line AA of FIG. 1.

As Shown, the probe according to the invention, for ultrasonic scanning at low depth consists of a tubular body 1 that is rigid and consists of a distal end and a proximal end extended by a tip of the probe 2 in the form of a concave body, a partitioning element 3 arranged in the tubular body 1 at a distance from the proximal end, and a main chamber 4 that is airtight in which a liquid for acoustic coupling is introduced, for example, water, and in which is arranged an assembly for emission and reception 5 of an given frecuency. This assembly for the emission and reception is mounted affixed on a mount 6 itself slidably mounted on two rectilinear guides 7 mounted in the main chamber 4. This mount 6 is driven in the main chamber in an alternating rectilinear translation movement in a direction perpendicular to the direction of the acoustic beam emitted by the assembly for emission and reception 5 in the direction of an acoustic slot 8 that is arranged in the tip of the probe and is extending in a perpendicular manner to the direction of the acoustic beam. This acoustic slot 8 is advantageously made of a wall having a very small thickness. It can be made of a flexible thermoformable membrane and is affixed to the tip of the probe so as to totally block a rectangular opening made in the wall of the tip of the probe, perpendicularly to the direction of the acoustic beam. By the flexible membrane, the tip of the probe is applied against the anatomical region to be scanned. This probe tip can be affixed in an immobile manner to the tubular body.

The assembly for emission and reception is made up of an electroacoustic monotransducer of the piezo-electric type, consisting of a head for emitting and receiving ultrasonic waves. The head is located at a distance of several millimeters from the acoustic slot.

The mount 6 is mobilized along the alternating translation movement by a transmission of movement united with the rotary output shaft of an electric motor 9 installed in a secondary chamber 10 arranged in the tubular body 1 behind the partitioning element 3.

In the preferred embodiment form; the mount 6 consists of a parallelopios block made of a synthetic material that has a low water absorption power.

Advantageously, the mount 6 is made of polyethylene, this material having good properties of mechanical resistance, while having a low density. The low weight of the mount 6 makes it possible to limit the effects of imbalance. The mount has an axial threaded hole that goes through it in which the threaded shaft of a tubular support is introduced, which receives the electroacoustic monotransducer in fixation.

In the preferred embodiment form, the mount extends in alternating translation in a hollowed out area going through a support 11 that is united with the partitioning element 3. This support 11 is affixed by several screws to the partitioning element 3. According to the preferred embodiment form, the hollowed out area passing through is limited by two support banks that are parallel and opposite, and the guides 7, parallel between them, and the acoustic slot 8, are mounted in grooves made in a hollowed V in the parallel banks. These guides are extending beyond their groove, in a manner to be able to receive the slidable mount 6. The mount 6 also contains two grooves made in shapes by which it is slidable engaged on the guides 7.

The guides 7, made in a manner likely to resist corrosion of water, are in a cylindrical form. Preferably, these guides 7 are made of stainless steel.

According to the preferred embodiment form, the transmission of the movement between the mount 6 and the rotary output shaft of the motor 9 consists of a crankpin 12 carried in an eccentric manner by a plate 13 that is united with a drive shaft 14 coupled by any known mechanism to the rotary output shaft of the motor 9. This transmission also consists of a slide 15, in the form of a groove having a U-shaped cross section, formed in the mount 6 perpendicular to the guides 7. The crankpin 12, in the form of a cylinder, is slidably engaged, with very little play in the slide 15. Thus, it is thought that by rotation of the assembly made of the shaft 14, the plate 13 and the crankpin 12, the alternating displacement of the mount 6 is obtained. According to the preferred embodiment, the frequency of the alternating rectilinear movement is 10 Hz.

In order to prevent any unbalancing effect, due to the presence of the crankpin 12, a balancing plate is formed in the plate 13 by removing material.

In the preferred embodiment form the partitioning element 3 is made of a cylindrical tubular sheath equipped at a distance from its two ends with a median transverse partition 16. This partition extends perpendicularly to the longitudinal axis of the partitioning element 3. The external diameter of the tubular cylindrical sheath is very slightly less than the internal diameter of the tubular body in a manner that this sheath can adjust in a sliding manner in the partitioning element 3. At least one annular airtight joint 3a is interposed between the tubular sheath and the tubular body. In the partition 16, a median cylinder bore is made that goes through in which an airtight guide bearing 17 is rotatably mounted the drive shaft 14. This airtight bearing is advantageously made up of an airtight ball bearing.

The airtight bearing 17, in combination with the transverse partition 16 of the partitioning element 3 and the airtight seal 3a, ensures the airtightedness of the main chamber, which eliminates the risk of the flow of water towards the secondary chamber.

At a distance from the airtight bearing 16, the drive shaft is rotatably mounted on a cylindrical guide bore that passes through and is made in a collar 18 installed in the hole that goes through a wall of the cover 19 affixed against the rear part of the partitioning element 3.

Advantageously, in the goal of synchronizing the position of the assembly for the emission and reception with the shooting, a detector is provided having an angular position 20 coupled to the drive shaft 14. This detector 20 is fitted to emit, in the form of an electric pulse, a signal that represents a particular angular value and corresponds to a precise redefined position of the assembly for the emission and reception of acoustic waves.

From this signal, the shot is set off, i.e. the emission of an ultrasonic wave train.

Preferably, the detector 20 is installed in the partitioning element 3 between the wall of the cover 19 and the median wall. Purely as a guideline is example, the angular position detector is of the HALL effect type and contains a collar with magnet(s) affixed in rotation and translation on the shaft 14 and a support carrying the detector itself, affixed against the median wall.

The probe as described can also be used in order to reconstitute the images in three dimensions. For this purpose, to the probe according to the invention, a guide support can be connected that ensures its guiding either along a translation movement in a direction perpendicular to the direction of alternating movement of the monotransducer, or along a pivoting movement along an axis parallel to the direction of movement of the monotransducer.

Figure 3:
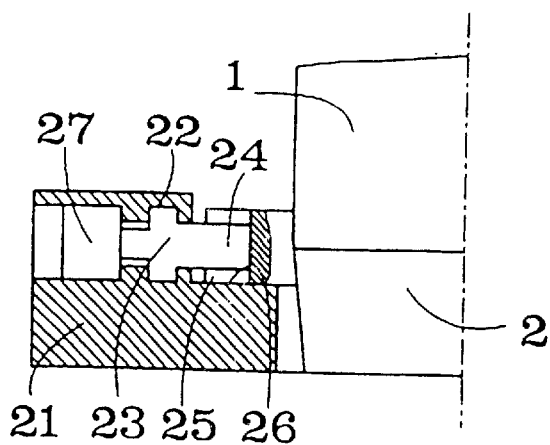
FIG. 3 is a partial half section view of a support for a probe.
Figure 4:
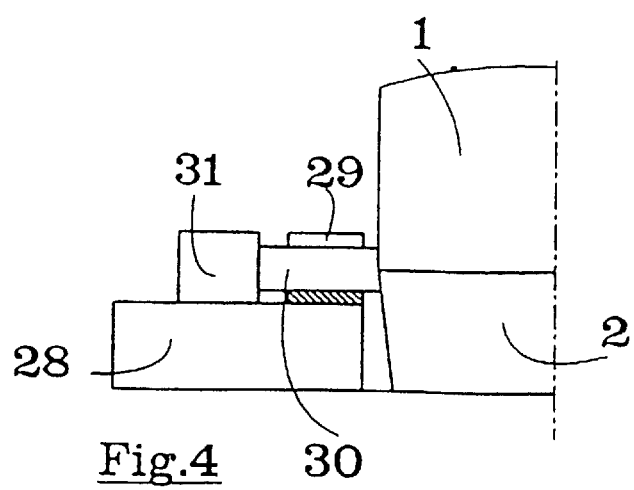
FIG. 4 is a partial half section view of another type of support for a probe.

In FIG. 3, a guide support according to a first embodiment form is shown. This guide support has a hollowed-out frame 21 forming a frame by which it is affixed on the anatomical region to be observed. Along both opposite sides, the frame contains two rectilinear parallel slides 22, with which two guide blocks 23 act together in guiding, each provided perpendicularly to the guide direction that the slide defines, with an adjustment wedge slug 24 that has a polygonal cross-section. The adjustment wedge slugs 24 extend towards each other parallel to the plane that defines the frame. With each of these adjustment wedge slugs 24, a fitting acts together in the form of a fork 25 that is united with the tip of the probe 2 and designed to come against a surface plane 26 that forms an indentation, this surface plane being parallel to the plane that defines the frame. Relative to the surface plane, the fork defines a plane by which it is led to slide on this surface. The two forks 25 that the tip of the probe has extend in a direction parallel to the direction of movement of the monotransducer. In addition, each plane is contained in a plane perpendicular to the direction of propagation of the ultrasonic wave. In creating a support plane on the plane with the corresponding indentation, the plane ensures the support of the probe in a specified direction by which the direction of propagation of the ultrasonic wave is normal to the plane that defines the frame. By this position, the longitudinal axis of the probe is normal to the plane of the frame. Connected to one of the guide blocks 23 is a linear position sensor 27 emitting in the form of an electric signal, information representative of the position of the probe along the slides.

With the support as described, the probe is moved manually in translation along the slides of the support frame. Also, a support could be provided that is equipped with motor mechanisms ensuring the motorization of the probe displacement. These motor mechanisms can be made by at least one movement transmission made up of two pulleys on which a same belt winds around, whose upper section is affixed to one of the guide blocks. One of the pulleys is supported on the output shaft of the electric drive motor. Preferably, two transmissions for movement are provided, which cooperate respectively with the two guide blocks.

According to another embodiment form, the support is made up entirely of a hollowed-out support frame 28 that has on two opposite sides, two bearings 29 in the form of a fork in which two swivel pins 30 are engaged radially opposite united with the tip of the probe 2 and extending in a common direction parallel to the axis of movement of the monotransducer. Coupled to one of these swivel pins is an angular sensor 31. The support, by the frame, is affixed against the anatomical region to be scanned. The probe can swing around the axis defined by the two swivel pins 30.

It goes without saying that the invention presented here can have any adjustments and variations in the domain of equivalent techniques without necessarily leaving the frame of the present patent.

We claim:

1. A scanning probe apparatus for scanning an anatomical region comprising:
   a tubular body having a main chamber and a secondary chamber;
   an ultrasonic wave means positioned in said main chamber for emitting and receiving an ultrasonic wave, said ultrasonic wave means comprising an acoustic microtransducer, said ultrasonic wave means affixed to a mount;
   a drive means mounted in said secondary chamber, said drive means for driving said mount in a back-and-forth movement in said main chamber;
   a partitioning element affixed in said tubular body and separating said main chamber from said secondary chamber;
   a probe tip blocking said main chamber in an airtight manner, said probe tip being of a solid material and having an acoustic slot, said solid material being permeable to the ultrasonic wave emitted by said acoustic microtransducer toward the anatomical region and permeable to the ultrasonic wave reflected by the anatomical region back toward said acoustic micro transducer; and
   an acoustic coupling liquid contained in said main chamber, said solid material of said probe tip being impermeable to said acoustic coupling liquid, the back-and-forth movement being in parallel translation to said acoustic slot of said probe tip, said ultrasonic wave being normal to said acoustic slot.

2. The apparatus of claim 1, said ultrasonic wave means being separated by a distance from said acoustic slot, said distance being equal to or greater than:

$$P_{max} \cdot C1/C2$$

where:
   Pmax=maximum depth of scanning
   C1=speed of the ultrasonic wave in the acoustic coupling liquid; and
   C2=speed of the ultrasonic wave in the anatomical region.

3. The apparatus of claim 1, said acoustic coupling liquid being water.

4. The apparatus of claim 1, said mount being mounted in sliding relation on a pair of parallel rectilinear guides, said pair of parallel rectilinear guides being parallel to said acoustic slot.

5. The apparatus of claim 4, further comprising:
   transmission means for transmitting a movement of said drive means to said mount, said transmission means comprising a crankpin carried eccentrically by a plate, said drive means comprising a motor having a rotary output shaft, said plate being united by a drive shaft to said rotary output shift, said mount having a slide formed therein perpendicular to said pair of parallel rectilinear guides, said crankpin being engaged in sliding relation in said slide.

6. The apparatus of claim 5, said plate having a balancing plane.

7. The apparatus of claim 4, said mount positioned in a hollowed-out area formed in a support united with said partitioning element, said hollowed-out area having two support banks parallel and opposite to each other, said pair of parallel rectilinear guides being respectively mounted in two grooves formed in a V-shaped groove in the respective two support banks, said mount having a pair of V-shaped grooves slidably engaged respectively on said pair of parallel rectilinear guides.

8. The apparatus of claim 5, said partitioning element being a tubular sheath having a median transverse partition with a central bore, said drive shaft supported in said central bore by an airtight guide bearing.

9. The apparatus of claim 8, said drive shaft being rotatably mounted in a cylindrical guide bore of a collar, said collar mounted in a hole extending through a wall of a cover affixed against a rear part of said partitioning element.

10. The apparatus of claim 5, further comprising:
    detection means coupled to said drive shaft, said detection means for detecting an angular position.

* * * * *